United States Patent [19]

Höltmann et al.

[11] Patent Number: 4,900,717

[45] Date of Patent: Feb. 13, 1990

[54] RECOVERY OF 2,6-DIALKYL-NAPHTHALENE ISOMERS

[75] Inventors: Wilhelm Höltmann, Munster; Robert Zellerhoff, Hamminkeln; Rudolf Oberkobusch, Duisburg; Peter Stäglich, Kempen; Bernhard Charpey, Mülheim an der Ruhr, all of Fed. Rep. of Germany

[73] Assignee: Rutgerswerke AG, Fed. Rep. of Germany

[21] Appl. No.: 152,430

[22] Filed: Feb. 4, 1988

Related U.S. Application Data

[63] Continuation of Ser. No. 901,182, Aug. 27, 1986, abandoned.

[30] Foreign Application Priority Data

Sep. 4, 1985 [DE] Fed. Rep. of Germany ....... 3531559

[51] Int. Cl.$^4$ ................................................ C07C 7/14
[52] U.S. Cl. ..................................... 505/812; 585/813; 585/817
[58] Field of Search ............... 585/812, 813, 814, 815, 585/817

[56] References Cited

U.S. PATENT DOCUMENTS

| | | | |
|---|---|---|---|
| 3,202,726 | 8/1965 | Malmberg et al. | 260/674 |
| 3,235,615 | 2/1966 | Allen et al. | 260/668 |
| 3,400,548 | 9/1968 | Drayer | 62/58 |
| 3,485,885 | 12/1969 | Peterkin et al. | 260/674 |
| 3,590,091 | 6/1971 | Skarada et al. | 260/674 |
| 3,798,280 | 3/1974 | Shimada et al. | 260/668 F |

FOREIGN PATENT DOCUMENTS 730740  3/1966  Canada ................................. 585/812

*Primary Examiner*—Glenn Caldarola
*Attorney, Agent, or Firm*—Jordan B. Bierman

[57] ABSTRACT

In a process for selective crystallization of 2,6-dialkyl-naphthalene selected from the group consisting of methyl-n-propyl-naphthalene, methyl isopropyl-naphthalene, ethyl-isopropyl-napthalene, ethyl-n-butyl-naphthalene, di-n-propyl-naphthalene, diisopropyl-naphthalene, methyl-amyl-naphthalene, ethyl-amyl-naphthalene, propyl-amyl-naphthalene, di-n-butyl-naphthalene and diisobutyl-naphthalene from their isomer mixtures from a polar solvent solution, the improvement comprising effecting the crystallization with constant stirring at a temperature from 25° to −30° C. to obtain the 2,6-dialkyl-naphthalene at least 95% pure.

8 Claims, No Drawings

RECOVERY OF 2,6-DIALKYL-NAPHTHALENE ISOMERS

PRIOR APPLICATION

This application is a continuation of copending U.S. patent application Ser. No. 901,182 filed Aug. 27, 1986, now abandoned.

STATE OF THE ART 2,6-dialkyl-naphthalenes are useful starting products for the preparation of 2,6-naphthalene dicarboxylic acid, the acid component of thermally particularly stable condensation polymers and an isomer product of the highest purity is needed especially for this purpose. 2,6-dialkyl-naphthalenes are obtained by alkylation of naphthalene resulting in a mixture with numerous isomers with a content of 2,6-dialkyl-naphthalene in this isomer mixture between 5 and 50%, depending on the alkylation process. To obtain a technical grade product by conventional separation and purification methods, 2,6-dialkyl-naphthalenes must be previously concentrated to a content of approx. 80 to 90%. Special care must be taken that the 1, 5-dialkyl-naphthalene is not concentrated also during this step, since an economical separation of the pure 2,6-dialkyl-naphthalene is impossible in the presence of the former isomer in concentration exceeding 5%. A largely complete and early separation of 1,5-dialkyl-naphthalene is desirable for this reason and especially the 2,7-, 1,3- and 1,6-isomers must also be separated. This separation is not readily possible with conventional methods and an economical preparation of technical grade 2,6-dialkyl-naphthalene is consequently not available.

OBJECT OF THE INVENTION

It is an object of the invention to provide an economical process for the recovery of technical grade 2,6-dialkyl-naphthalenes from an isomer mixture containing 1,5-isomers as well as other isomers.

This and other objects and advantages of the invention will become obvious from the following detailed description.

THE INVENTION

In the novel process of the invention for selective crystallization of 2,6-dialkyl-naphthalenes selected from the group consisting of methyl-n-propyl-naphthalene, methylisopropyl-naphthalene, methyl-n-butyl-naphthylene, methyl-isobutyl-naphthalene, ethyl-iso-propyl-naphthalene, ethyl-n-butyl-naphthalene, di-n-propyl-naphthalene, diisopropyl-naphthalene, methyl-amyl-naphthalene, ethyl-amyl-naphthalene, propyl-amyl-naphthalene, di-n-butyl-naphthalene and diisobutyl-naphthalene from their isomer mixtures from a polar solvent solution, the improvement comprises effecting the crystallization with constant stirring at a temperature from 25° to −30° C.

Dialkyl-naphthalene fractions obtained by conventional alkylation and transalkylation methods have isomer distributions by weight in the following order of magnitude:

| | |
|---|---|
| 1,3-dialkyl-naphthalene | 5-34% |
| 1,5-dialkyl-naphthalene | 1-12% |
| 1,6-dialkyl-naphthalene | 1-15% |
| 1,7-dialkyl-naphthalene | 1-29% |
| 2,6-dialkyl-naphthalene | 12-36% |
| 2,7-dialkyl-naphthalene | 9-35% |

Specific mixtures are given in the examples. Dialkyl-naphthalenes that can be worked up according to the invention are methyl-n-propyl-naphthalene, methylisopropyl-naphthalene, methyl-n-butyl-naphthalene, methylisobutyl-naphthalene, ethylisopropyl-naphthalene, ethyl-n-butyl-naphthalene, di-n-propyl-naphthalene, diisopropyl-naphthalene, methylamyl-naphthalene, ethylamyl-naphthalene, propylamyl-naphthalene, di-n-butyl-naphthalene, or diisobutyl-naphthalene, preferably methylisopropyl-naphthalene and diisopropyl-naphthalenes that are technical interesting for the preparation of especially thermally stable poly-condensates.

When such a diisopropyl-naphthalene fraction, given as an example, is subjected to the step-by-step cold crystallization normally used for isomer separation with seeding of the fraction with the respective pure products, 24% crystal material in which the 1,3- and 1,7-isomers are concentrated to approx. 70%, can be filtered off after 96 hours. After an additional period of 7 days at −15° C., an additional amount of 6% crystal material containing also 1% of 1,5- and 26% 1,3-diisopropyl-naphthalene besides 67% of 2,6-diisopropyl-naphthalene is obtained. No pure 2,6-diisopropyl-naphthalene can be isolated economically be conventional methods of solvent or melting crystallization.

A commercial preparation is also impossible because of the long crystallization times. While lowering the final cooling temperature to −25° or −30° C. does increase the crystal yield to 8-12%, the desired crystal fraction contains in addition to 77% of 2,6- also 12% of 1,5-isomer. The separation of the two isomers in this composition is impossible by conventional separation methods on a commercial scale since the 1,5-isomer is concentrated by it.

These trials also revealed that the precipitation of 2,6-diisopropyl-naphthalene is accelerated by shaking or repeated, brief stirring. But the observation was made that the concentration of 1,5-diisopropyl-naphthalene in the crystal material also rises to values exceeding 12%.

The precipitation with the aid of alcohol for the separation of 2,6- from 2,7-diisopropyl-naphthalene, known from Chem. Abs. Vol. 85: 5423e, resulted in a shortened crystallization time and simultaneously in a good yield. The observation was made that a fraction with concentrated 2,6-diisopropyl-naphthalene precipitates initially from mixtures of a diisopropyl-naphthalene fraction with a polar solvent at a ratio of 1:0.5 to 4.0 upon cooling and that an economically feasible yield of 8 to 12% of crude crystal material is obtained in 24 to 48 hours at a temperature of −10° to −20° C. But the 1,5-isomer also becomes concentrated in the crystal material with this procedure and concentrations of 12 to 30% of 1,5-diisopropyl-naphthalene in the crystal material are obtained when these precipitations are performed with occasional stirring.

Thus, it is surprising that the cold crystallization of dialkyl-naphthalene fractions with a polar solvent under constant stirring in the temperature range from room temperature to −30° C. yields, depending on the respective 2,6-isomer content of the fraction used, crystals with contents of 85 to 95% of 2,6-dialkyl-naphthalene and up to 2% maximum of 1,5-dialkyl-naphthalene to produce a technical grade 2,6-dialkyl-naphthalene with contents of 95–99% after one reprecipitation.

Usable as polar solvents are low molecular weight alcohols such as alkanols like ethanol, propanol or isopropanol and ketones such as acetone, methyl ethyl ketone or methylisobutyl ketone as well as low molecular chlorinated hydrocarbons such as chloroform or methylene chloride. The amount of solvent used is in the range from 0.5 to 5.0 preferably at 1 to 2 parts by weight for each part by weight of dialkyl-naphthalene fraction.

The solution consisting of dialkyl-naphthalene fraction and solvent is cooled with constant stirring. It is important that the solution or dispersion is constantly kept in motion to guarantee the optimal formation of the desired crystallization nuclei. But the stirring shall not be much above the critical number of rotations of the stirrer since the preferred precipitation of the 2,6-isomer is then impeded. The optimal stirrer movement lies in the range of the critical number of rotations of the stirrer. On the other hand, the movement of the mixture is needed only from the onset of crystallization. But since this is not a fixed point and, on the other hand, an earlier onset of crystallization is induced by the movement of the mixture, agitation of the mixture from the start of the cooling phase is recommended. The cooling of the mixture may be continuous or step wise, and optimal results are obtained with continuous cooling at cooling rates in the range from 2° to 15° C./hour, preferably from 2° to 5° C./hour.

For dialkyl-naphthalene fractions with a content of 2,6-isomers below 30%, the cooling temperature is preferably in the range from 0° to −20° C., with higher contents in the range from 20° to 0° C. The seeding of the precooled mixture before the onset of crystallization with pure 2,6-dialkyl-naphthalene is advantageous for a further acceleration of the precipitation.

The precipitated crystal material is separated from the mother liquor by mechanical means, preferably with a centrifuge. The main component 2,6-dialkyl-naphthalene can then be easily purified by conventional crystallization methods to yield a highly pure product (>99%). The process of the invention permits in principle the preparation of 2,6-dialkyl-naphthalene from isomer mixtures having a 2,6-isomer content of 10% and more.

In the following examples there are described several preferred embodiments to illustrate the invention. However, it should be understood that the invention is not intended to be limited to the specific embodiments.

EXAMPLE 1

5,000 parts by weight of an isomer mixture of the following composition of the main isomers of 16% of 1,3-diisopropyl-naphthalene 5% of 1,5-diisopropyl-naphthalene, 17% of 1,7-diisopropyl-naphthalene 20% of 2,6-diisopropyl-naphthalene and 17% 2,7-diisopropyl-naphthalene were mixed at room temperature with 2,500 parts by weight of 99% ethanol and the mixture was cooled to −10° C. over 4 hours with constant stirring. Then, the mixture was seeded with 0.2 parts by weight of pure 2,6-diisopropyl-naphthalene and cooled to −20° C. over the next three hours with constant stirring which sufficiency is intensive that no crystals deposit in the crystallization vessel. After filtration 330 parts by weight of a crude crystal material of the following composition 86% of 2,6-diisopropyl-naphthalene, 3% of 2.7-diisopropyl-naphthalene, 3% of 1,3-diisopropyl-naphthalene, 2% of 1,5-diisopropyl-naphthalene and 6% of residual isomers were obtained.

The ethanol was removed from the mother liquor by distillation and returned to the crystallization step and the residual isomer mixture was used for another purpose. The crude crystal material was purified further by fractionated melting or solvent crystallization obtain pure 2,6-diisopropyl-naphthalene.

EXAMPLE 2

2,500 parts by weight of an isomer mixture as in Example 1 were mixed with 3,750 parts by weight of isopropanol at room temperature and the mixture was cooled to −11° C. over 3½ hours, with constant stirring. Then, the mixture was seeded with 0.2 parts by weight of pure 2,6-diisopropyl-naphthalene and cooled to −20° C. over another three hours with constant stirring. After another two hours at −20° C. 151 parts by weight of a crude crystal material with the following composition were obtained after the separation of the crystal material: 89% of 2,6-diisopropyl-naphthalene, 5% of 2,7-diisopropyl-naphthalene, 1% of 1,5-diisopropyl-naphthalene, 1% of 1,3-diisopropyl-naphthalene and 4% of residual isomers.

The isopropanol was removed from the remaining filtrate by distillation and the residual isomer mixture was used for another purpose. The crude crystal material was further purified by melting or solvent crystallization to obtain pure 2,6-diisopropyl-naphthalene.

EXAMPLE 3

290 parts by weight of an methyl isopropyl-naphthalene isomer mixture with a content of 46% of 2-methyl-6-isopropyl-naphthalene, 39% of 2-methyl-7-isopropyl-naphthalene and 15% of residual isomers were mixed with 435 parts by weight of 99% ethanol at room temperature as in Example 1 and cooled to −10° C. over 8 hours with constant stirring. Then, the mixture was mixed with 0.2 parts by weight of pure 2-methyl-6-isopropyl-naphthalene and cooled over an additional 5-hour period to −20° C. with constant stirring. During this, 32 parts by weight of a crude crystal material precipitated which were separated from ethanol by filtration. The composition of the crude crystal material was 95% of 2-methyl-6-isopropyl-naphthalene, 3% of 2-methyl-7-isopropyl-naphthalene and 2% of residual isomers. The filtrate was freed of ethanol by distillation and the remaining isomer mixture was used for another purpose. The crude crystal material was further purified by fractionated melting or solvent crystallization to obtain pure 2-methyl-6-isopropyl-naphthalene.

COMPARISON EXAMPLE 1

175 parts by weight of an isomer mixture of the following composition of the main isomers: 15% of 1,3-diisopropyl-naphthalene, 6% of 1,5-diisopropyl-naphthalene, 17% of 1,7-diisopropyl-naphthalene, 20% of 2,6-diisopropyl-naphthalene and 17% of 2,7-diisopropyl-naphthalene were cooled to −15° C. and held at this temperature for 96 hours. The precipitated crystal material was separated and 41.3 parts by weight of a crude crystal material with a content of 71% of 1,3- and 1,7-diisopropyl-naphthalene, 27% of 2,6-diisopropyl-naphthalene and 2% of residual isomers were obtained. After an additional period of 168 hours at 15° C., 10.7 parts by weight of additional crystal material were obtained with the composition: 67% of 2,6-diisopropyl-naphthalene, 5% of 2,7-diisopropyl-naphthalene, 26% of 1,3-diisopropyl-naphthalene and 2% of 1,5-diisopropyl-naphthalene.

COMPARISON EXAMPLE 2

600 parts by weight of an isomer mixture of the same composition as in Comparison Example 1 were cooled to −25° C. with stirring and after 97 hours at 25° C., 19.4 parts by weight of a crude crystal material with the following composition were obtained: 71% of 2,6-diisopropyl-naphthalene, 6% of 2,7-diisopropyl-naphthalene and 23% of 1,5-diisopropyl-naphthalene. After an additional period of 96 hours at −25° C., an additional 21.3 g of crude crystal material with largely 44% of 2,6-diisopropyl-naphthalene and 30% of 1,5-diisopropyl-naphthalene were obtained.

COMPARISON EXAMPLE 3

2,000 parts by weight of an isomer mixture as in Comparison Example 1 were mixed with 5,000 parts by weight of 99% of ethanol and cooled at −30° C. for 120 hours. 357 parts by weight of a crude crystal material which was largely 61% of 2,6-, 19% of 1,5- and 8% of 2,7-diisopropyl-naphthalene were obtained.

COMPARISON EXAMPLE 4

2,500 parts by weight of an isomer mixture as in Comparison Example 1 were mixed with 3,750 parts by weight of 99% ethanol and cooled to −15° C. After 25.7 hours with stirring for 5 minutes each at intervals of 30 minutes, 146 parts by weight of a crude crystal material of the following composition: 77% of 2,6-diisopropyl-naphthalene, 19% of 1,5-diisopropyl-naphthalene, 2% of 2,7-diisopropyl-naphthalene and 2% of residual isomers were obtained.

Various modifications of the process of the invention may be made without departing from the spirit or scope thereof and it should be understood that the invention is intended to be limited only as defined in the appended claims.

What we claim is:

1. In a process for selective crystallization of 2,6-dialkyl-naphthalenes selected from the group consisting of methyl-n-propyl-naphthalene, methyl-isopropyl-naphthalene, methyl-n-butyl-naphthalene, methyl-isobutyl-naphthalene, ethyl-isopropyl-naphthalene, ethyl-n-butyl-naphthalene, di-n-propyl-naphthalene, diisopropyl-naphthalene, di-n-butyl-naphthalene and diisobutyl-naphthalene from their isomeric mixtures from a polar solvent solution at a temperature of 25° to −30° C., the improvement comprising effecting the crystallization with constant stirring to obtain the 2,6-dialkyl naphthalene in a high degree of purity.

2. The process of claim 1 wherein the ratio of isomer mixture to solvent lies in the range from 1 to 0.5–4.0.

3. The process of claim 1 wherein the ratio of isomer mixture to solvent lies in the range from 1 to 2.

4. The process of claim 1 wherein the cooling rate is 2° to 15° C. per hour.

5. The process of claim 1 wherein the dissolved isomer mixture is cooled with stirring at a cooling rate of 2° to 15° C. per hour, and pure 2,6-dialkyl-naphthalene is used to seed the solution before the beginning of crystallization.

6. The process of claim 1 wherein the 2,6-isomer is obtained from dialkyl-naphthalene mixture with a 2,6-dialkyl-naphthalene content of more than 10% by weight.

7. The process of claim 1 wherein 2,6-diisopropyl-naphthalene is obtained in the presence of 1,5-diisopropyl-naphthalene.

8. The process of claim 1 wherein 2-isopropyl-6-methyl-naphthalene is obtained.

* * * * *